(12) United States Patent
Mignogna et al.

(10) Patent No.: US 10,005,860 B2
(45) Date of Patent: Jun. 26, 2018

(54) CATALYST COMPONENTS FOR THE POLYMERIZATION OF OLEFINS

(71) Applicant: Basell Poliolefine Italia S.r.l., Milan (IT)

(72) Inventors: Alessandro Mignogna, Ferrara (IT); Reynald Chevalier, Frankfurt (DE); Igor Kashulin, Moscow (RU); Ilya Nifant'ev, Moscow (RU); Giampiero Morini, Ferrara (IT); Martin Schneider, Hochheim (DE)

(73) Assignee: Basell Poliolefine Italia S.r.l., Milan (IT)

( * ) Notice: Subject to any disclaimer, the term of this patent is extended or adjusted under 35 U.S.C. 154(b) by 0 days. days.

(21) Appl. No.: 15/428,940

(22) Filed: Feb. 9, 2017

(65) Prior Publication Data

US 2017/0166667 A1 Jun. 15, 2017

Related U.S. Application Data

(62) Division of application No. 14/891,949, filed as application No. PCT/EP2014/059938 on May 15, 2014, now Pat. No. 9,644,051.

(30) Foreign Application Priority Data

May 17, 2013 (EP) .................... 13168358

(51) Int. Cl.
| | | |
|---|---|---|
| C08F 110/06 | (2006.01) | |
| C07C 327/26 | (2006.01) | |
| C07C 327/28 | (2006.01) | |
| C07C 329/10 | (2006.01) | |
| C07C 333/04 | (2006.01) | |

(52) U.S. Cl.
CPC .......... *C08F 110/06* (2013.01); *C07C 327/26* (2013.01); *C07C 327/28* (2013.01); *C07C 329/10* (2013.01); *C07C 333/04* (2013.01)

(58) Field of Classification Search
None
See application file for complete search history.

(56) References Cited

U.S. PATENT DOCUMENTS

| | | |
|---|---|---|
| 5,034,481 A | 7/1991 | Funk et al. |
| 5,780,378 A | 7/1998 | Toida et al. |
| 5,877,265 A | 3/1999 | Toida et al. |
| 6,245,868 B1 | 6/2001 | Agapiou et al. |
| 7,388,061 B2 | 6/2008 | Gao et al. |
| 2001/0012496 A1 | 8/2001 | Agapiou et al. |
| 2001/0020072 A1 | 9/2001 | Agapiou et al. |
| 2011/0130530 A1 | 6/2011 | Coalter, III et al. |
| 2011/0282013 A1 | 11/2011 | Baita et al. |
| 2013/0245306 A1 | 9/2013 | Coalter, III et al. |
| 2013/0261273 A1 | 10/2013 | Chen et al. |
| 2014/0275456 A1 | 9/2014 | Xu et al. |

FOREIGN PATENT DOCUMENTS

| | | |
|---|---|---|
| CN | 105339085 A | 2/2016 |
| EP | 2192133 A1 | 6/2010 |
| JP | S58142340 A | 8/1983 |
| JP | 2005517746 A | 6/2005 |
| RU | 2144041 C1 | 1/2000 |
| WO | WO-9961486 A1 | 12/1999 |
| WO | WO-2008022900 A1 | 2/2008 |
| WO | WO-2010076289 A1 | 7/2010 |
| WO | WO-2011068770 A1 | 6/2011 |
| WO | WO-2012088028 A1 | 6/2012 |

*Primary Examiner* — Catherine S Branch

(57) ABSTRACT

Catalyst component for the polymerization of olefins comprising Mg, Ti and an electron donor of formula (I)

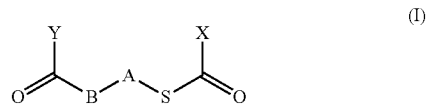

In which X and Y are selected from, $R^1$, and $-OR^1$ and $-NR_2$, B is oxygen or sulphur S is sulphur, $R^1$ is selected from $C_1$-$C_{15}$ hydrocarbon groups, optionally contain a heteroatom selected from halogen, P, S, N, O and Si, which can be fused together to form one or more cycles, R is hydrogen or $R^1$ and A is a bivalent bridging group with chain length between the two bridging bonds being 1-10 atoms.

11 Claims, No Drawings

CATALYST COMPONENTS FOR THE POLYMERIZATION OF OLEFINS

This application is a Divisional Application that claims benefit to U.S. Non-Provisional application Ser. No. 14/891,949, filed Nov. 17, 2015, that is the U.S. National Phase of PCT International Application PCT/EP2014/059938, filed May 15, 2014, claiming priority of European Patent Application No. 13168358.3, filed May 17, 2013, the contents of which are incorporated herein by reference in its entirety.

FIELD OF THE INVENTION

The present disclosure relates to the field of chemistry. In particular it relates to catalyst components for the polymerization of olefins, in particular propylene, comprising a Mg dihalide based support on which are supported Ti atoms and an electron donor selected from a specific class of mercaptoalcohol derivatives. The present disclosure further relates to the catalysts obtained from said components and to their use in processes for the polymerization of olefins in particular propylene.

BACKGROUND OF THE INVENTION

Catalyst components for the stereospecific polymerization of olefins are widely known in the art. Concerning the polymerization of propylene, the most spread out catalyst family belongs to the Ziegler-Natta category and in general terms it comprises a solid catalyst component, constituted by a magnesium dihalide on which are supported a titanium compound and an internal electron donor compound, used in combination with an Al-alkyl compound. Conventionally however, when a higher crystallinity of the polymer is required, also an external donor (for example an alkoxysilane) is needed in order to obtain higher isotacticity. One of the preferred classes of internal donors is constituted by the esters of phthalic acid, diisobutylphthalate being the most used. The phthalates are used as internal donors in combination with alkylalkoxysilanes as external donor. This catalyst system gives good performances in terms of activity, isotacticity and xylene insolubility.

One of the problems associated with the use of this catalyst system is that the phthalates have recently raised concerns due to the medical issues associated with their use and some compounds within this class have been classified as source of heavy health problems.

Consequently, research activities have been devoted to discover alternative classes of internal donors for use in the preparation of catalyst components for propylene polymerization.

Internal donors are described in U.S. Pat. No. 7,388,061 and WO2010/078494 which both relate to esters of aliphatic or aromatic diols. Both the references do not describe possible alternatives to these structures. Moreover, in view of the fact that their basic structure is that of a diol, it is difficult to produce multifunction derivatives with different functional groups (ester/ether, ester/carbamate etc) because the two oxygens of the diol basic structure have identical reactivity.

Surprisingly, the applicant has found that a particular class of donors based on mercapto derivatives is suited to generate a wide arrange of molecules with equal or different functional groups which when used as internal donors generate catalysts showing an excellent balance of activity and stereospecificity.

SUMMARY OF THE INVENTION

Accordingly, it is provided a catalyst component for the polymerization of olefins comprising Mg, Ti and an electron donor compound of formula (I)

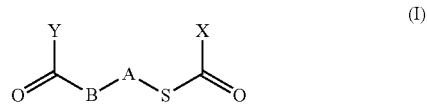

In which X and Y are selected from, $R^1$, and $-OR^1$ and $-NR_2$, B is oxygen or sulphur S is sulphur, $R^1$ is selected from $C_1$-$C_{15}$ hydrocarbon groups, optionally contain a heteroatom selected from halogen, P, S, N, O and Si, which can be fused together to form one or more cycles, R is hydrogen or $R^1$ and A is a bivalent bridging group with chain length between the two bridging bonds being 1-10 atoms.

DETAILED DESCRIPTION OF THE INVENTION

In case of cyclic structures acting as bridging groups the term "chain length" is referred to the shortest sequence of atoms bridging the two sulphur or oxygen/sulfur atoms of formula (I). In some embodiments, the bridging group has formula $-(ZR^2_m)_n-$ in which, independently, Z is selected from C, Si, Ge, O, N, S or P, the $R^2$ groups, equal to or different from each other, are hydrogen or a $C_1$-$C_{20}$ hydrocarbon radicals, optionally containing a heteroatom selected from halogen, P, S, N, O and Si, which can be fused together to form one or more cycles, m is a number satisfying the valences of Z and n is an integer ranging from 1 to 10. In certain embodiments, for the bridging group having the formula $-(ZR^2_m)_n-$ the atoms O, S, and N are not directly linked to the S or O of formula (I), i.e. O, S, and N are not the terminal atoms of the bridging group. In some embodiments, Z is selected from C and Si. In further embodiments, Z is carbon.

In a particular embodiment, the said bivalent bridging group is selected from the group consisting of aliphatic, alicyclic and aromatic bivalent radicals, optionally substituted with $C_1$-$C_{15}$ hydrocarbon groups and/or with heteroatoms selected from halogen, P, S, N, O and Si, and having a bridging chain length ranging from 1 to 6 atoms including 1 to 4 atoms.

In some embodiments, the bridging group is an aliphatic or alicyclic bridging group having a bridging chain length of 2-3 carbon atoms. Among this class, bridging groups may include those of formula $-(CR^3_p)_s-$ in which $R^3$ is independently hydrogen or a $C_1$-$C_{20}$ hydrocarbon radicals, optionally substituted with heteroatoms selected from halogen, P, S, N, O and Si, which can be fused together to form one or more cycles, p is a number satisfying the available valence of carbon and s is a number from 1 to 6 including from 1 to 4. Examples of bridging groups are methyliden, ethane-1,2-diyl, butane-2,3-diyl, pentane-2,4-diyl, 2,2-diisobutylpropane-1,3-diyl, cyclohexane-1,2-diyl, cyclopentane-1,2-diyl.

A subclass for use in the present technology is that of formula (II) below:

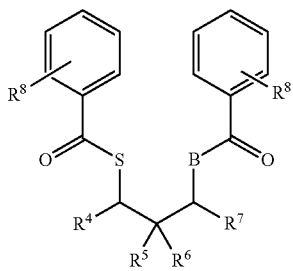
(II)

in which B is sulfur or oxygen in which $R^4$-$R^7$ groups, equal to or different from each other, are hydrogen or $C_1$-$C_{15}$ hydrocarbon groups, optionally containing an heteroatom selected from halogen, P, S, N and Si, and $R^8$ equal to or different from each other, are selected from $C_1$-$C_{15}$ hydrocarbon groups which can be optionally linked to form a cycle and n is an integer from 0 to 5.

B in formula (II) may be sulfur, $R^4$ and $R^7$ are selected from $C_1$-$C_{10}$ alkyl groups including $C_1$-$C_5$ alkyl groups such as methyl, and $R^5$ and $R^6$ are selected from hydrogen or $C_1$-$C_{10}$ alkyl groups. $R^8$ groups are independently selected from $C_1$-$C_{10}$ alkyl groups such as methyl, ethyl, n-propyl and n-butyl. The index n can vary from 0 to 5 inclusive, including from 1 to 3. When n is 1, the substituent $R^8$ may reside in position 4 of the benzoate ring.

Another bridging group for use in the present technology is the one based on cyclic aromatic groups which through the carbon ring atoms can link the two sulphur or sulphur/oxygens atoms of formula (I). Among them, the phenyl groups, optionally substituted with halogens or $C_1$-$C_{20}$ alkyl radicals, bridging the oxygen atoms in position 1,2 or 1,3 or 1,4 and the naphthalene groups, optionally substituted bridging the oxygen groups in position 1,2 or 2,3 or 1,8 may be used.

Among them, the structure of formula (III) below:

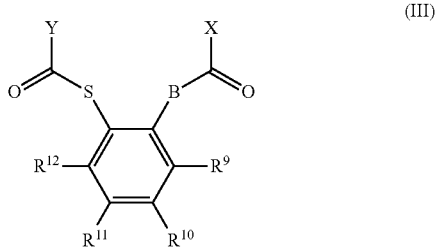
(III)

in which X, Y and B have the same meaning specified in claim 1, and $R^9$-$R^{12}$ independently, are selected from hydrogen, halogens or $C_1$-$C_{15}$ hydrocarbon groups optionally substituted with heteroatoms selected from halogen, P, S, N, O and Si may be used in accordance with the present technology.

Structures of formula (III) are those in which the groups $R^9$, $R^{11}$ and/or $R^{12}$ are $C_1$-$C_5$ alkyl groups including those in which $R^9$ and/or $R^{12}$ are a primary alkyl group such as methyl, and $R^{11}$ is a tertiary alkyl group such as tert-butyl.

Specific examples are 1,2-phenylene, 3-methyl-1,2-phenylene, 4-chloro-1,2-phenylene, 4-(tert-butyl)-1,2-phenylene, 3,6-dimethyl-1,2-phenylene, 3,5-dimethyl-1,2-phenylene, 5-(tert-butyl)-3-methyl-1,2-phenylene, 3,5-diisopropyl-1,2-phenylene, naphthalene-1,8-diyl, naphthalene-1,2-diyl, naphthalene-2,3-diyl groups.

In some embodiments, B in formulas (I) and (III) is oxygen. Moreover, $R^1$ groups are selected from $C_1$-$C_{10}$ alkyl groups and $C_6$-$C_{15}$ aryl or alkylaryl groups including linear $C_1$-$C_5$ alkyl groups such as methyl, ethyl and propyl while aryl or alkylaryl groups are phenyl groups including those substituted with halogen and/or $C_1$-$C_5$ alkyl groups.

Possibilities of combinations between X and Y groups of formulae (I) and (III) are those in which B is O, X is $R^1$ and Y is selected from the group consisting of $R^1$, —$OR^1$ and —$NR_2$ in which $R^1$ and R have the meanings explained above. In some embodiments both X and Y are selected from $R^1$ and in particular from $C_6$-$C_{15}$ aryl or alkylaryl groups. Another combination is that in which B is O, X is —$OR^1$ and Y is selected from —$NR_2$ and —$OR^1$. According to a further embodiment, B is O, X is a —$R^1$ group selected from $C_6$-$C_{15}$ aryl or alkylaryl groups and Y is —$OR^1$ in which $R^1$ is selected from $C_1$-$C_{10}$ alkyl group.

In the —$NR_2$ groups the R radicals are selected from $C_1$-$C_{10}$ alkyl groups including linear $C_1$-$C_5$ alkyl groups such as methyl, ethyl and propyl.

The final amount of electron donor compound in the solid catalyst component may range from 1 to 25% by weight preferably in the range from 3 to 20% by weight.

Non limiting examples of structures of formulas (I) and (II) are the following: 2-(benzoylthio)-4-(tert-butyl)-3,6-dimethylphenyl benzoate, 2-(benzoylthio)-4-(tert-butyl)-6-methylphenyl benzoate, 4-(tert-butyl)-2-((3-chlorobenzoyl) thio)-3,6-dimethylphenyl 3-chlorobenzoate, 4-(tert-butyl)-2-((3-chlorobenzoyl)thio)-6-methylphenyl 3-chlorobenzoate, 4-(tert-butyl)-2-((diethylcarbamoyl)thio)-3,6-dimethylphenyl benzoate, 4-(tert-butyl)-2-((diethylcarbamoyl)thio)-6-methylphenyl benzoate, 4-(tert-butyl)-2-((dimethylcarbamoyl)thio)-3,6-dimethylphenyl benzoate, 4-(tert-butyl)-2-((dimethylcarbamoyl)thio)-6-methylphenyl benzoate, 4-(tert-butyl)-2-methyl-6-((4-propylbenzoyl)thio) phenyl 4-propylbenzoate, 4-(tert-butyl)-3,6-dimethyl-2-((4-propylbenzoyl)thio)phenyl 4-propylbenzoate, S-(3-(tert-butyl)-6-((diethylcarbamoyl)oxy)-2,5-dimethylphenyl) benzothioate, S-(3-(tert-butyl)-6-((dimethylcarbamoyl) oxy)-2,5-dimethylphenyl) benzothioate, S-(5-(tert-butyl)-2-((diethylcarbamoyl)oxy)-3-methylphenyl) benzothioate, S-(5-(tert-butyl)-2-((dimethylcarbamoyl)oxy)-3-methylphenyl) benzothioate, 4-(tert-butyl)-2-((diethylcarbamoyl)thio)-3,6-dimethylphenyl diethylcarbamate, 4-(tert-butyl)-2-((di ethylcarbamoyl)thio)-6-methylphenyl diethylcarbamate, 4-(tert-butyl)-2-((dimethylcarbamoyl)thio)-3,6-dimethylphenyl dimethylcarbamate, 4-(tert-butyl)-2-((dimethylcarbamoyl)thio)-6-methylphenyl dimethylcarbamate, 4-(tert-butyl)-2-((ethoxycarbonyl)thio)-3,6-dimethylphenyl ethyl carbonate, 4-(tert-butyl)-2-((ethoxycarbonyl)thio)-6-methylphenyl ethyl carbonate, S,S'-(4-(tert-butyl)-3,6-dimethyl-1,2-phenylene) dibenzothioate, S,S'-(4-(tert-butyl)-3-methyl-1,2-phenylene) dibenzothioate, S-(3-(tert-butyl)-6-((diethylcarbamoyl)thio)-2,5-dimethylphenyl) benzothioate, S-(3-(tert-butyl)-6-((diethylcarbamoyl)thio)-2-methylphenyl) benzothioate, S-(3-(tert-butyl)-6-((ethoxycarbonyl) thio)-2,5-dimethylphenyl) benzothioate, S-(3-(tert-butyl)-6-((ethoxycarbonyl)thio)-2-methylphenyl) benzothioate, S-(4-(tert-butyl)-2-((diethylcarbamoyl)thio)-3,6-dimethylphenyl) benzothioate, S-(4-(tert-butyl)-2-((diethylcarbamoyl)thio)-3-methylphenyl) benzothioate, S-(4-(tert-butyl)-2-((ethoxycarbonyl)thio)-3,6-dimethylphenyl) benzothioate, S-(4-(tert-butyl)-2-((ethoxycarbonyl)thio)-3-methylphenyl) benzothioate, S,S'-(4-(tert-butyl)-3,6-dimethyl-1,2-phenylene) O,O'-diethyl dicarbonothioate, S,S'-(4-(tert-butyl)-

3,6-dimethyl-1,2-phenylene) bis(diethylcarbamothioate), S,S'-(4-(tert-butyl)-3-methyl-1,2-phenylene) O,O'-diethyl dicarbonothioate, S,S'-(4-(tert-butyl)-3-methyl-1,2-phenylene) bis(diethylcarbamothioate), S-(3-(tert-butyl)-6-((ethoxycarbonyl)thio)-2,5-dimethylphenyl) diethylcarbamothioate, S-(3-(tert-butyl)-6-((ethoxycarbonyl)thio)-2-methylphenyl) diethylcarbamothioate, S-(4-(tert-butyl)-2-((ethoxycarbonyl)thio)-3,6-dimethylphenyl) diethylcarbamothioate, S-(4-(tert-butyl)-2-((ethoxycarbonyl)thio)-3-methylphenyl) diethylcarbamothioate, S,S'-(4-(tert-butyl)-3,6-dimethyl-1,2-phenylene) bis(4-propylbenzothioate), S,S'-(4-(tert-butyl)-3,6-dimethyl-1,2-phenylene) bis(3-chlorobenzothioate), 4-((diethylcarbamoyl)thio)pentan-2-yl benzoate, 4-((ethoxycarbonyl)thio)pentan-2-yl benzoate, 4-(benzoylthio)pentan-2-yl benzoate, S,S'-pentane-2,4-diyl dibenzothioate, S-(4-((diethylcarbamoyl)oxy)pentan-2-yl) benzothioate, S-(4-((diethylcarbamoyl)thio)pentan-2-yl) benzothioate, S-(4-((ethoxycarbonyl)oxy)pentan-2-yl) benzothioate, S-(4-((ethoxycarbonyl)thio)pentan-2-yl) benzothioate, 4-((diethylcarbamoyl)thio)pentan-2-yl diethylcarbamate, 4-((ethoxycarbonyl)thio)pentan-2-yl diethylcarbamate, 4-((ethoxycarbonyl)thio)pentan-2-yl ethyl carbonate, O,O'-diethyl S,S'-pentane-2,4-diyl dicarbonothioate, S,S'-pentane-2,4-diyl bis(diethylcarbamothioate), S-(4-((ethoxycarbonyl)oxy)pentan-2-yl) diethylcarbamothioate, S-(4-((ethoxycarbonyl)thio)pentan-2-yl) diethylcarbamothioate, 4-((3-chlorobenzoyl)thio)pentan-2-yl 3-chlorobenzoate, 4-((diethylcarbamoyl)thio)pentan-2-yl 3-chlorobenzoate, 4-((ethoxycarbonyl)thio)pentan-2-yl 3-chlorobenzoate, S,S'-pentane-2,4-diyl bis(3-chlorobenzothioate), S-(4-((diethylcarbamoyl)oxy)pentan-2-yl) 3-chlorobenzothioate, S-(4-((diethylcarbamoyl)thio)pentan-2-yl) 3-chlorobenzothioate, S-(4-((ethoxycarbonyl)oxy)pentan-2-yl) 3-chlorobenzothioate, S-(4-((ethoxycarbonyl)thio)pentan-2-yl) 3-chlorobenzothioate, 4-((diethylcarbamoyl)thio)pentan-2-yl diethylcarbamate, 4-((ethoxycarbonyl)thio)pentan-2-yl diethylcarbamate, 4-((ethoxycarbonyl)thio)pentan-2-yl ethyl carbonate, O,O'-diethyl S,S'-pentane-2,4-diyl dicarbonothioate, S,S'-pentane-2,4-diyl bis(diethylcarbamothioate), S-(4-((ethoxycarbonyl)oxy)pentan-2-yl) diethylcarbamothioate, S-(4-((ethoxycarbonyl)thio)pentan-2-yl) diethylcarbamothioate, 4-((4-propylbenzoyl)thio)pentan-2-yl 4-propylbenzoate, 4-((diethylcarbamoyl)thio)pentan-2-yl 4-propylbenzoate, 4-((ethoxycarbonyl)thio)pentan-2-yl 4-propylbenzoate, S,S'-pentane-2,4-diyl bis(4-propylbenzothioate), S-(4-((diethylcarbamoyl)oxy)pentan-2-yl) 4-propylbenzothioate, S-(4-((diethylcarbamoyl)thio)pentan-2-yl) 4-propylbenzothioate, S-(4-((ethoxycarbonyl)oxy)pentan-2-yl) 4-propylbenzothioate, S-(4-((ethoxycarbonyl)thio)pentan-2-yl) 4-propylbenzothioate, 4-((diethylcarbamoyl)thio)pentan-2-yl diethylcarbamate, 4-((ethoxycarbonyl)thio)pentan-2-yl diethylcarbamate, 4-((ethoxycarbonyl)thio)pentan-2-yl ethyl carbonate, O,O'-diethyl S,S'-pentane-2,4-diyl dicarbonothioate, S,S'-pentane-2,4-diyl bis(diethylcarbamothioate), S-(4-((ethoxycarbonyl)oxy)pentan-2-yl) diethylcarbamothioate, S-(4-((ethoxycarbonyl)thio)pentan-2-yl) diethylcarbamothioate, 2-((diethylcarbamoyl)thio)cyclohexyl benzoate, 2-((ethoxycarbonyl)thio)cyclohexyl benzoate, 2-(benzoylthio)cyclohexyl benzoate, S,S'-cyclohexane-1,2-diyl dibenzothioate, S-(2-((diethylcarbamoyl)oxy)cyclohexyl) benzothioate, S-(2-((diethylcarbamoyl)thio)cyclohexyl) benzothioate, S-(2-((ethoxycarbonyl)oxy)cyclohexyl) benzothioate, S-(2-((ethoxycarbonyl)thio)cyclohexyl) benzothioate, 2-((diethylcarbamoyl)thio)cyclohexyl diethylcarbamate, 2-((ethoxycarbonyl)thio)cyclohexyl diethylcarbamate, 2-((ethoxycarbonyl)thio)cyclohexyl ethyl carbonate, S,S'-cyclohexane-1,2-diyl O,O'-diethyl dicarbonothioate, S,S'-cyclohexane-1,2-diyl bis(diethylcarbamothioate), S-(2-((ethoxycarbonyl)oxy)cyclohexyl) diethylcarbamothioate, S-(2-((ethoxycarbonyl)thio)cyclohexyl) diethylcarbamothioate, 2-((3-chlorobenzoyl)thio)cyclohexyl 3-chlorobenzoate, 2-((diethylcarbamoyl)thio)cyclohexyl 3-chlorobenzoate, 2-((ethoxycarbonyl)thio)cyclohexyl 3-chlorobenzoate, S,S'-cyclohexane-1,2-diyl bis(3-chlorobenzothioate), S-(2-((diethylcarbamoyl)oxy)cyclohexyl) 3-chlorobenzothioate, S-(2-((diethylcarbamoyl)thio)cyclohexyl) 3-chlorobenzothioate, S-(2-((ethoxycarbonyl)oxy)cyclohexyl) 3-chlorobenzothioate, S-(2-((ethoxycarbonyl)thio)cyclohexyl) 3-chlorobenzothioate, 2-((diethylcarbamoyl)thio)cyclohexyl diethylcarbamate, 2-((ethoxycarbonyl)thio)cyclohexyl diethylcarbamate, 2-((ethoxycarbonyl)thio)cyclohexyl ethyl carbonate, S,S'-cyclohexane-1,2-diyl O,O'-diethyl dicarbonothioate, S,S'-cyclohexane-1,2-diyl bis(diethylcarbamothioate), S-(2-((ethoxycarbonyl)oxy)cyclohexyl) diethylcarbamothioate, S-(2-((ethoxycarbonyl)thio)cyclohexyl) diethylcarbamothioate, 2-((4-propylbenzoyl)thio)cyclohexyl 4-propylbenzoate, 2-((diethylcarbamoyl)thio)cyclohexyl 4-propylbenzoate, 2-((ethoxycarbonyl)thio)cyclohexyl 4-propylbenzoate, S,S'-cyclohexane-1,2-diyl bis(4-propylbenzothioate), S-(2-((diethylcarbamoyl)oxy)cyclohexyl) 4-propylbenzothioate, S-(2-((diethylcarbamoyl)thio)cyclohexyl) 4-propylbenzothioate, S-(2-((ethoxycarbonyl)oxy)cyclohexyl) 4-propylbenzothioate, S-(2-((ethoxycarbonyl)thio)cyclohexyl) 4-propylbenzothioate, 2-((diethylcarbamoyl)thio)cyclohexyl diethylcarbamate, 2-((ethoxycarbonyl)thio)cyclohexyl diethylcarbamate, 2-((ethoxycarbonyl)thio)cyclohexyl ethyl carbonate, S,S'-cyclohexane-1,2-diyl O,O'-diethyl dicarbonothioate, S,S'-cyclohexane-1,2-diyl bis(diethylcarbamothioate), S-(2-((ethoxycarbonyl)oxy)cyclohexyl) diethylcarbamothioate, S-(2-((ethoxycarbonyl)thio)cyclohexyl) diethylcarbamothioate, 8-((diethylcarbamoyl)thio)naphthalen-1-yl benzoate, 8-((ethoxycarbonyl)thio)naphthalen-1-yl benzoate, 8-(benzoylthio)naphthalen-1-yl benzoate, S,S'-naphthalene-1,8-diyl dibenzothioate, S-(8-((diethylcarbamoyl)oxy)naphthalen-1-yl) benzothioate, S-(8-((diethylcarbamoyl)thio)naphthalen-1-yl) benzothioate, S-(8-((ethoxycarbonyl)oxy)naphthalen-1-yl) benzothioate, S-(8-((ethoxycarbonyl)thio)naphthalen-1-yl) benzothioate, 8-((diethylcarbamoyl)thio)naphthalen-1-yl diethylcarbamate, 8-((ethoxycarbonyl)thio)naphthalen-1-yl diethylcarbamate, 8-((ethoxycarbonyl)thio)naphthalen-1-yl ethyl carbonate, O,O'-diethyl S,S'-naphthalene-1,8-diyl dicarbonothioate, S,S'-naphthalene-1,8-diyl bis(diethylcarbamothioate), S-(8-((ethoxycarbonyl)oxy)naphthalen-1-yl) diethylcarbamothioate, S-(8-((ethoxycarbonyl)thio)naphthalen-1-yl) diethylcarbamothioate, 8-((3-chlorobenzoyl)thio)naphthalen-1-yl 3-chlorobenzoate, 8-((diethylcarbamoyl)thio)naphthalen-1-yl 3-chlorobenzoate, 8-((ethoxycarbonyl)thio)naphthalen-1-yl 3-chlorobenzoate, S,S'-naphthalene-1,8-diyl bis(3-chlorobenzothioate), S-(8-((diethylcarbamoyl)oxy)naphthalen-1-yl) 3-chlorobenzothioate, S-(8-((diethylcarbamoyl)thio)naphthalen-1-yl) 3-chlorobenzothioate, S-(8-((ethoxycarbonyl)oxy)naphthalen-1-yl) 3-chlorobenzothioate, S-(8-((ethoxycarbonyl)thio)naphthalen-1-yl) 3-chlorobenzothioate, 8-((diethylcarbamoyl)thio)naphthalen-1-yl diethylcarbamate, 8-((ethoxycarbonyl)thio)naphthalen-1-yl diethylcarbamate, 8-((ethoxycarbonyl)thio)naphthalen-1-yl ethyl carbonate, O,O'-diethyl S,S'-naphthalene-1,8-diyl dicarbonothioate, S,S'-naphthalene-1,8-diyl bis(diethylcarbamothioate), S-(8-((ethoxycarbonyl)oxy)naphthalen-1-yl) diethylcarbamothioate, S-(8-((ethoxycarbonyl)thio)naphthalen-1-yl) diethylcarbamothioate, 8-((4-propylbenzoyl)thio)naphthalen-1-yl 4-propylbenzoate, 8-((diethylcarbamoyl)thio)naphthalen-1-yl 4-propylbenzoate, 8-((ethoxycarbonyl)thio)naphthalen-1-yl 4-propylbenzoate, S,S'-naphthalene-1,8-diyl bis(4-propylbenzothioate), S-(8-((diethylcarbamoyl)oxy)naphthalen-1-yl) 4-propylbenzothioate, S-(8-((diethylcarbamoyl)thio)naphthalen-1-yl) 4-propylbenzothioate, S-(8-((ethoxycarbonyl)oxy)naphthalen-1-yl) 4-propylbenzothioate, S-(8-((ethoxycarbonyl)thio)naphthalen-1-yl) 4-propylbenzothioate, 8-((diethylcarbamoyl)thio)naphthalen-1-yl diethylcarbamate, 8-((ethoxycarbonyl)thio)naphthalen-1-yl diethylcarbamate, 8-((ethoxycarbonyl)thio)naphthalen-1-yl ethyl carbonate, O,O'-diethyl S,S'-naphthalene-1,8-diyl dicarbonothioate, S,S'-naphthalene-1,8-diyl bis(diethylcarbamothioate), S-(8-((ethoxycarbonyl)oxy)naphthalen-1-yl) diethylcarbamothioate, S-(8-((ethoxycarbonyl)thio)naphthalen-1-yl) diethylcarbamothioate, (9-(((diethylcarbamoyl)thio)methyl)-9H-fluoren-9-yl)methyl benzoate, (9-(((ethoxycarbonyl)thio)methyl)-9H-fluoren-9-yl)methyl benzoate, (9-((benzoylthio)methyl)-9H-fluoren-9-yl)methyl benzoate, S,S'-((9H-fluorene-9,9-diyl)bis(methylene)) dibenzothioate, S-((9-(((diethylcarbamoyl)oxy)methyl)-9H-fluoren-9-yl)methyl) benzothioate, S-((9-(((diethylcarbamoyl)thio)methyl)-9H-fluoren-9-yl)methyl) benzothioate, S-((9-(((ethoxycarbonyl)oxy)methyl)-9H-fluoren-9-yl)methyl) benzothioate, S-((9-(((ethoxycarbonyl)thio)methyl)-9H-fluoren-9-yl)methyl) benzothioate, (9-(((diethylcarbamoyl)thio)methyl)-9H-fluoren-9-yl)methyl diethylcarbamate, (9-(((ethoxycarbonyl)thio)methyl)-9H-fluoren-9-yl)methyl diethylcarbamate, (9-(((ethoxycarbonyl)thio)methyl)-9H-fluoren-9-yl)methyl ethyl carbonate, S,S'-((9H-fluorene-9,9-diyl)bis(methylene)) O,O'-diethyl dicarbonothioate, S,S'-((9H-fluorene-9,9-diyl)bis(methylene)) bis(diethylcarbamothioate), S-((9-(((ethoxycarbonyl)oxy)methyl)-9H-fluoren-9-yl)methyl) diethylcarbamothioate, S-((9-(((ethoxycarbonyl)thio)methyl)-9H-fluoren-9-yl)methyl) diethylcarbamothioate.

As explained above, the catalyst components comprise, in addition to the above electron donors, Ti, Mg and halogen. In particular, the catalyst components comprise a titanium compound, having at least a Ti-halogen bond and the above mentioned electron donor compounds supported on a Mg halide. The magnesium halide may be $MgCl_2$ in active form, which is a support for Ziegler-Natta catalysts. U.S. Pat. No. 4,298,718 and U.S. Pat. No. 4,495,338 were the first to describe the use of these compounds in Ziegler-Natta catalysis. These patents describe magnesium dihalides in active form used as support or co-support in components of catalysts for the polymerization of olefins are characterized by X-ray spectra in which the most intense diffraction line that appears in the spectrum of the non-active halide is diminished in intensity and is replaced by a halo whose maximum intensity is displaced towards lower angles relative to that of the more intense line.

Titanium compounds for use in the catalyst component of the present disclosure are $TiCl_4$ and $TiCl_3$; furthermore, Ti-haloalcoholates of formula $Ti(OR)_{m-y}X_y$ can be used, where m is the valence of titanium, y is a number between 1 and m−1, X is halogen and R is a hydrocarbon radical having from 1 to 10 carbon atoms.

In a particular embodiment the amount of Ti atoms is higher than 2.5% wt including higher than 3.0% and in the range of 3.0 to 8% with respect to the total weight of said catalyst component.

The preparation of the solid catalyst component can be carried out according to several methods. One method comprises the reaction between magnesium alcoholates or chloroalcoholates (such as the chloroalcoholates prepared according to U.S. Pat. No. 4,220,554) and an excess of $TiCl_4$ in the presence of the electron donor compounds at a temperature of about 80 to 120° C.

According to a method of the present technology, the solid catalyst component can be prepared by reacting a titanium compound of formula $Ti(OR)_{m-y}X_y$, where m is the valence of titanium and y is a number between 1 and m, such as $TiCl_4$, with a magnesium chloride deriving from an adduct of formula $MgCl_2$·pROH, where p is a number between 0.1 and 6, including from 2 to 3.5, and R is a hydrocarbon radical having 1-18 carbon atoms. The adduct can be suitably prepared in spherical form by mixing alcohol and magnesium chloride in the presence of an inert hydrocarbon immiscible with the adduct, operating under stirring conditions at the melting temperature of the adduct (100-130° C.). Then, the emulsion is quickly quenched, thereby causing the solidification of the adduct in form of spherical particles. Examples of spherical adducts prepared according to this procedure are described in U.S. Pat. No. 4,399,054 and U.S. Pat. No. 4,469,648. The so obtained adduct can be directly reacted with Ti compound or it can be previously subjected to thermal controlled dealcoholation (80-130° C.) so as to obtain an adduct in which the number of moles of alcohol may be lower than 3, including between 0.1 and 2.5. The reaction with the Ti compound can be carried out by suspending the adduct (dealcoholated or as such) in cold $TiCl_4$ (around 0° C.); the mixture is heated up to 80-130° C. and kept at this temperature for 0.5-2 hours. The treatment with $TiCl_4$ can be carried out one or more times. The mercapto derivative electron donor compound may be added during the treatment with $TiCl_4$. The preparation of catalyst components in spherical form are described in European Patent Applications EP-A-395083, EP-A-553805, EP-A-553806, EPA601525 and WO98/44001.

The solid catalyst components obtained according to the above method show a surface area (by B.E.T. method) between 20 and 500 $m^2/g$ and preferably between 50 and 400 $m^2/g$, and a total porosity (by B.E.T. method) higher than 0.2 $cm^3/g$ including between 0.2 and 0.6 $cm^3/g$. The porosity (Hg method) due to pores with radius up to 10.000 Å may range from 0.3 to 1.5 $cm^3/g$, including from 0.45 to 1 $cm^3/g$. The solid catalyst component has an average particle size ranging from 5 to 120 m including from 10 to 100 m.

In any of these preparation methods the desired electron donor compounds can be added as such or, in an alternative way, it can be obtained in situ by using an appropriate precursor capable to be transformed in the desired electron donor compound.

Regardless of the preparation method used, the final amount of the electron donor compound of formula (I) is such that its molar ratio with respect to the Ti atoms is from 0.01 to 2, including from 0.05 to 1.2.

The solid catalyst components according to the present technology are converted into catalysts for the polymerization of olefins by reacting the components with organoaluminum compounds.

An object of the present technology may involve a catalyst for the polymerization of olefins $CH_2$=CHR, in which R is hydrogen or a hydrocarbyl radical with 1-12 carbon atoms, comprising the product obtained by contacting:

(i) the solid catalyst component as disclosed above and
(ii) an alkylaluminum compound and optionally,
(iii) an external electron donor compound The alkyl-Al compound (ii) may be chosen from among the trialkyl aluminum compounds such as for example triethylaluminum, triisobutylaluminum, tri-n-butylaluminum, tri-n-hexylaluminum, tri-n-octylaluminum. It is also possible to use alkylaluminum halides, alkylaluminum hydrides or alkylaluminum sesquichlorides, such as $AlEt_2Cl$ and $Al_2Et_3Cl_3$, possibly in mixture with the above cited trialkylaluminums.

External electron-donor compounds may include silicon compounds, ethers, esters, amines, heterocyclic compounds, including 2,2,6,6-tetramethylpiperidine and ketones.

Another class of external donor compounds is that of silicon compounds of formula $(R_7)_a(R_8)_bSi(OR_9)_c$, where a and b are integers from 0 to 2, c is an integer from 1 to 4 and the sum (a+b+c) is 4; $R_7$, $R_8$, and $R_9$, are radicals with 1-18 carbon atoms optionally containing heteroatoms. These compounds include silicon compounds in which a is 1, b is 1, c is 2, at least one of $R_7$ and $R_8$ is selected from branched alkyl, cycloalkyl or aryl groups with 3-10 carbon atoms optionally containing heteroatoms and $R_9$ is a $C_1$-$C_{10}$ alkyl group, in particular methyl. Examples of such silicon compounds are methylcyclohexyldimethoxysilane (C donor), diphenyldimethoxysilane, methyl-t-butyldimethoxysilane, dicyclopentyldimethoxysilane (D donor), diisopropyldimethoxysilane, (2-ethylpiperidinyl)t-butyldimethoxysilane, (2-ethylpiperidinyl)thexyldimethoxysilane, (3,3,3-trifluoro-n-propyl)(2-ethylpiperidinyl)dimethoxysilane, methyl(3,3,3-trifluoro-n-propyl)dimethoxysilane, N,N-diethylaminotriethoxysilane. Silicon compounds in which a is 0, c is 3, $R_8$ is a branched alkyl or cycloalkyl group, optionally containing heteroatoms, and $R_9$ is methyl may also be used. Examples of such silicon compounds are cyclohexyltrimethoxysilane, t-butyltrimethoxysilane and thexyltrimethoxysilane.

The electron donor compound (iii) is used in such an amount to give a molar ratio between the organoaluminum compound and said electron donor compound (iii) of from 0.1 to 500, preferably from 1 to 300 and from 3 to 100.

Therefore, it constitutes a further embodiment of this disclosure a process for the (co)polymerization of olefins $CH_2=CHR$, in which R is hydrogen or a hydrocarbyl radical with 1-12 carbon atoms, carried out in the presence of a catalyst comprising the product of the reaction between:
  (i) the solid catalyst component comprising Mg, Ti and an electron donor compound of formula (I) as above described;
  (ii) an alkylaluminum compound and,
  (iii) optionally an electron-donor compound (external donor).

The polymerization process can be carried out according to techniques such as slurry polymerization using as diluent an inert hydrocarbon solvent, or bulk polymerization using the liquid monomer (for example propylene) as a reaction medium. Moreover, it is possible to carry out the polymerization process in gas-phase operating in one or more fluidized or mechanically agitated bed reactors.

The polymerization may be carried out at temperature of from 20 to 120° C., including from 40 to 80° C. When the polymerization is carried out in gas-phase the operating pressure may be between 0.5 and 5 MPa, including between 1 and 4 MPa. In the bulk polymerization the operating pressure may be between 1 and 8 MPa, including between 1.5 and 5 MPa.

The following examples are given in order to illustrate the disclosure without limiting it.

EXAMPLES

Characterizations
  Determination of X.I.
  2.5 g of polymer and 250 ml of o-xylene were placed in a round-bottomed flask provided with a cooler and a reflux condenser and kept under nitrogen. The obtained mixture was heated to 135° C. and was kept under stirring for about 60 minutes. The final solution was allowed to cool to 25° C. under continuous stirring, and the insoluble polymer was then filtered. The filtrate was then evaporated in a nitrogen flow at 140° C. to reach a constant weight. The content of said xylene-soluble fraction is expressed as a percentage of the original 2.5 grams and then, by difference, the X.I. %.

Determination of Donors.
  The content of electron donor has been carried out via gas-chromatography. The solid component was dissolved in acidic water. The solution was extracted with ethyl acetate, an internal standard was added, and a sample of the organic phase was analyzed in a gas chromatograph, to determine the amount of donor present at the starting catalyst compound.

Melt Flow Rate (MFR)
  The melt flow rate MIL of the polymer was determined according to ISO 1133 (230° C., 2.16 Kg)

Ex 1. Synthesis of 2-(benzoylthio)-4-(tert-butyl)-3,6-dimethylphenyl benzoate

First Step. Synthesis of 4-(tert-butyl)-2-mercapto-3,6-dimethylphenol

The reaction is carried out in atmosphere of argon. The 4-tert-butyl-2,5-dimethylphenol (20 g, 0.11 mol) is dissolved in 120 mL of toluene, containing 0.37 g of sulfur. The solution of 4.9 mL (0.062 mol) of $S_2Cl_2$ in 50 mL of toluene is added slowly through the dropping funnel with continued efficient stirring at such rate that the reaction temperature does not exceed 30° C. When it is completed the solution is heated at 75° C. for 1 h and allowed to cool to room temperature The reaction mixture is concentrated under low vacuum to have a residue volume of about 60 mL. The suspension obtained is slowly added to a suspension of 5.38 g (0.14 mol) of $LiAlH_4$ in 180 mL of $Et_2O$.

The reaction mixture is refluxed for 6 h, stirred overnight and is carefully treated with 5% HCl. Organic solution is separated, aqueous layer is extracted with $Et_2O$ several times. The combined organic phase is dried over $MgSO_4$, evaporated and the residue is crystallized from heptane. Yield 5.76 g (49%).

Second Step. Synthesis of 2-(benzoylthio)-4-(tert-butyl)-3,6-dimethylphenyl benzoate The solution of 4-(tert-butyl)-2-mercapto-3,6-dimethylphenol (10 g, 0.048 mol) in toluene (290 mL) is treated sequentially with benzoyl chloride (11.8 mL, 0.10 mol) and $Et_3N$ (20.0 mL) at 0° C. After 16 h of stirring at room temperature, it is poured into aqueous HCl and is diluted with toluene (100 mL). The organic layer is washed sequentially with water, 2% aqueous NaOH, water, dried over $MgSO_4$, evaporated and the oil obtained is recrystallized from 95% EtOH (50 mL). Yield 15.5 g (78%).

Ex 2. Synthesis of 4-(tert-butyl)-2-((ethoxycarbonyl)thio)-6-methylphenyl ethyl carbonate First Step. Synthesis of 4-(tert-butyl)-2-mercapto-6-methylphenol The reaction is carried out in atmosphere of argon. The 4-tert-butyl-2-methylphenol (90 g, 0.5 mol) is dissolved in 250 mL of toluene, containing 0.5 g of sulfur. The solution of 22 mL (0.55 mol) of $S_2Cl_2$ in 100 mL of toluene is added slowly through the dropping funnel with continued efficient stirring at such rate that the reaction temperature does not exceed 30° C. Then the solution is heated at 75° C. for 1 h and allowed to cool to room temperature. The toluene is removed under low vacuum and the residue is dissolved in 200 mL of Et$_2$O. The solution obtained is slowly added to a suspension of 24 g (0.63 mol) of LiAlH$_4$ in 600 mL of Et$_2$O.

The reaction mixture is refluxed for 6 h, stirred overnight and carefully treated with 5% HCl. Organic layer is separated and aqueous layer is extracted with Et$_2$O several times. The combined organic phase is dried over MgSO$_4$, evaporated and distilled. Yield 50.1 g (47%).

Second Step. Synthesis of 4-(tert-butyl)-2-((ethoxycarbonyl)thio)-6-methylphenyl ethyl carbonate The solution of 4-(tert-butyl)-2-mercapto-6-methylphenol (7.88 g, 0.0342 mol) in toluene (150 mL) is treated sequentially with pyridine (12 mL) and ethyl chloroformate (7.19 mL, 0.0752 mol) with stirring and cooling (0° C.). After stirring at room temperature for 16 h the reaction mixture is treated with water and is diluted with toluene (100 mL). The organic layer is washed sequentially with aqueous HCl and water, dried over MgSO$_4$, evaporated and distilled in vacuum (165° C./0.5 mmHg). Yield 8.9 g (73%).

Ex 3. Synthesis of 4-(tert-butyl)-2-((ethoxycarbonyl)thio)-3,6-dimethylphenyl ethyl carbonate The procedure is the same as that used in the Ex 2 except that 4-(tert-butyl)-2-mercapto-3,6-dimethylphenol is used instead of 4-(tert-butyl)-2-mercapto-6-methylphenol. After distillation yield of 73%.

Ex 4. One-pot synthesis of 4-(tert-butyl)-2-((diethylcarbamoyl)thio)-6-methylphenyl 3-chlorobenzoate The solution of 4-(tert-butyl)-2-mercapto-6-methylphenol (9.82 g, 0.05 mol) in pyridine (40 mL) is treated in 30 min with diethylcarbamoyl chloride (7.0 g, 0.05 mol) at stirring and cooling (−30° C.). After stirring at room temperature for 16 h, the reaction mixture is treated with 3-chlorobenzoyl chloride (9.1 g, 0.05 mol) also with stirring and cooling (0° C.). After stirring at room temperature for additional 16 h, the reaction mixture is poured into the water-ice mixture containing 80 mL of conc. HCl. Then it is extracted with CH$_2$Cl$_2$ and the organic phase is washed sequentially with aqueous HCl, water, 5% solution of NaOH, water and dried over MgSO$_4$ and concentrated. The product is purified by column chromatography on neutral Al$_2$O$_3$ with using of toluene/hexane mixture (1/2) as eluent. Yield 10.0 g (46%).

Ex 5. One-pot synthesis of 4-(tert-butyl)-2-((dimethylcarbamoyl)thio)-6-methylphenyl 3-chlorobenzoate The procedure is the same as that used in the Ex 4 except that dimethylcarbamoyl chloride is used instead of diethylcarbamoyl chloride. Yield 72%.

Ex 6. One-pot synthesis of S-(5-(tert-butyl)-2-((ethoxycarbonyl)oxy)-3-methylphenyl) dimethylcarbamothioate The procedure is the same as that used in the Ex 4 except that ethyl chloroformate is used instead of 3-chlorobenzoyl chloride. Yield 59%.

Ex 7. One-pot synthesis of S-(5-(tert-butyl)-2-((ethoxycarbonyl)oxy)-3-methylphenyl) diethylcarbamothioate The procedure is the same as that used in the Ex 6 except that diethylcarbamoyl chloride is used instead of dimethylcarbamoyl chloride. Yield 57%.

Ex 8. One-pot synthesis of 4-(tert-butyl)-2-((ethoxycarbonyl)thio)-3,6-dimethylphenyl 3-chlorobenzoate The solution of 4-(tert-butyl)-2-mercapto-6-methylphenol (9.0 g, 0.043 mol) and pyridine (16 mL) in toluene (160 mL) is treated in 3 h with a solution of ethyl chloroformate (4.64 g, 0.043 mol) in toluene (30 mL) at stirring and cooling (0° C.). After stirring at room temperature for 16 h, the reaction mixture is treated with 3-chlorobenzoyl chloride (7.53 g, 0.043 mol) also at stirring and cooling (0° C.). After 16 h of stirring at room temperature, it is poured at the shaking into aqueous HCl and is diluted by toluene (100 mL). The organic layer is washed sequentially with water, 2% aqueous NaOH, water, dried over MgSO$_4$, evaporated and the oil obtained is recrystallized from petroleum ether. Yield 11.6 g (64%).

Ex 9. One-pot synthesis of 4-(tert-butyl)-2-((ethoxycarbonyl)thio)-3,6-dimethylphenyl benzoate The procedure is the same as that used in the Ex 8 except that benzoyl chloride is used instead of 3-chlorobenzoyl chloride. Yield after crystallization from heptane is 54%.

Ex 10. One-pot synthesis of 4-(tert-butyl)-2-((ethoxycarbonyl)thio)-3,6-dimethylphenyl 4-methylbenzoate The procedure is the same as that used in the Ex 8 except that 4-methylbenzoyl chloride is used instead of 3-chlorobenzoyl chloride. Yield after crystallization from petroleum ether is 56%.

Ex 11. One-pot synthesis of 4-(tert-butyl)-2-((ethoxycarbonyl)thio)-6-methylphenyl 3-chlorobenzoate The procedure is the same as that used in the Ex 8 except that 4-(tert-butyl)-2-mercapto-6-methylphenol is used instead of 4-(tert-butyl)-2-mercapto-3,6-dimethylphenol. Yield after crystallization from petroleum ether is 46%.

Ex 12. One-pot synthesis of 4-(tert-butyl)-2-((ethoxycarbonyl)thio)-6-methylphenyl benzoate The procedure is the same as that used in the Ex 9 except that 4-(tert-butyl)-2-mercapto-6-methylphenol is used instead of 4-(tert-butyl)-2-mercapto-3,6-dimethylphenol. Yield after crystallization from mixture of petroleum ether/CHCl$_3$ (about 1/1) is 34%.

Ex 13. One-pot synthesis of 4-(tert-butyl)-2-((ethoxycarbonyl)thio)-6-methylphenyl 4-methylbenzoate The procedure is the same as that used in the Ex 10 except that 4-(tert-butyl)-2-mercapto-6-methylphenol is used instead of 4-(tert-butyl)-2-mercapto-3,6-dimethylphenol. Yield after crystallization from petroleum ether is 38%.

Ex 14. One-pot synthesis of 4-(tert-butyl)-2-((ethoxycarbonyl)thio)-3,6-dimethylphenyl furan-2-carboxylate The procedure is the same as that used in the Ex 11 except that 2-furoyl chloride is used instead of 3-chlorobenzoyl chloride. Yield after crystallization from petroleum ether and EtOH is 56%.

Ex 15. One-pot synthesis of 4-(tert-butyl)-2-((ethoxycarbonyl)thio)-6-methylphenyl diethylcarbamate A solution of 4-(tert-butyl)-2-mercapto-6-methylphenol (18.83 g, 0.096 mol) and pyridine (27 mL) in toluene (350 mL) was treated in 4 h with a solution of ethyl chloroformate (9.15 mL, 0.097 mol) in toluene (50 mL) under stirring and cooling (0° C.). After stirring at room temperature for 16 h, the mixture was treated with diethylcarbamoyl chloride (20 mL, 0.158 mol) and $Et_3N$ (20 mL) also under stirring and cooling (0° C.). After 48 h of stirring at room temperature, it was quenched with aqueous HCl and was diluted with toluene (100 mL). The organic layer was washed with water, dried over $MgSO_4$, evaporated and the residue obtained was distilled in vacuum (180-182° C./0.3 mmHg). Yield 8.4 g (24%).

Ex 16. Synthesis of S-(5-cyclohexyl-2-((ethoxycarbonyl)oxy)-3-methylphenyl) dimethylcarbamothioate First Step: Synthesis of 4-cyclohexyl-2-mercapto-6-methylphenol A solution of $S_2Cl_2$ (20 mL, 0.25 mol) in toluene (250 mL) was treated with a solution of 4-cyclohexyl-2-methylphenol (47.6 g, 0.25 mol) in toluene (250 mL) under stirring. After addition the solution was stirred for additional 2 h. The solvent was evaporated under vacuum, the residue was dissolved in 95% EtOH (400 mL), then zinc powder was added (50 g, 0.79 mol) followed by concentrated HCl added dropwise (190 mL) at 0° C. and stirring. After addition the mixture was stirred for additional 2 h. The reaction mixture was poured into water (900 mL) and was extracted with $CH_2Cl_2$ several times. The combined organic phase was dried over $MgSO_4$, evaporated and the residue was distilled under vacuum (133-136° C./0.5 mmHg). Yield 26.7 g (48%).

Second Step. Synthesis of S-(5-cyclohexyl-2-((ethoxycarbonyl)oxy)-3-methylphenyl) dimethylcarbamothioate A solution of 4-cyclohexyl-2-mercapto-6-methylphenol (16.68, 0.075 mol) and pyridine (19 mL) in toluene (180 mL) was treated in 30 min with dimethylcarbamoyl chloride (8.47 g, 0.082 mol) under stirring and cooling (0° C.). After stirring at room temperature for 16 h, the reaction mixture was treated with ethyl chloroformate (9.77 mL, 0.09 mol) also under stirring and cooling (0° C.). After stirring at room temperature for additional 16 h, the reaction mixture was poured into a water-ice mixture containing 30 mL of conc. HCl. Then it was extracted with $CH_2Cl_2$, the organic phase was washed sequentially with aqueous HCl and water, dried over $MgSO_4$, evaporated and the residue was distilled under vacuum (212-215° C./0.4 mmHg). Yield 11.4 g (42%).

Ex 17. Synthesis of syn S,S'-pentane-2,4-diyl dibenzothioate

First Step: Synthesis of syn-pentane-2,4-diyl bis(4-methylbenzenesulfonate)

A 250 mL reaction vessel is charged with syn 2,4-pentanediol (10 g, 95.1 mmol) and pyridine (70 g). The mixture is cooled to −10° C. and p-toluenesulfonyl chloride (40.3 g, 2.2 eq) is slowly added. The mixture is allowed to stir at ambient temperature for 15 h. Ethyl acetate (100 mL) is added to the reaction mixture and the resulting organic layer is washed with a saturated aqueous $NH_4Cl$ solution and a saturated aqueous NaCl solution, then dried over $MgSO_4$, filtered and concentrated on a rotary evaporator which resulted in the crude product as a hell yellow solid.

Second Step: Synthesis of syn S,S'-pentane-2,4-diyl dibenzothioate

A 100 mL reaction vessel is charged with syn pentane-2,4-diyl bis(4-methylbenzenesulfonate) (5.6 g, 13.4 mmol), benzenecarbothioic S-acid (4.13 g, 2 eq), $NaHCO_3$ (2.28 g, 2 eq) and DMF (25 mL). The mixture is allowed to stir at 80° C. for 2 h. The red solution is diluted with ethyl acetate (50 mL) and the resulting solution is washed with a saturated aqueous $NaHCO_3$ solution and a saturated aqueous NaCl solution. The organic layer is dried over $MgSO_4$, filtered and concentrated on a rotary evaporator which resulted in the crude product as a red oil. It is purified by means of chromatography ($SiO_2$)-cyclohexane/ethyl acetate: 40/1. Yield: 2 g (43.3%).

Ex 18. Synthesis of S,S'-pentane-2,4-diyl bis(4-propylbenzothioate)

First Step: Synthesis of S,S'-pentane-2,4-diyl diethanethioate

A 250 mL reaction vessel is charged with pentane-2,4-diyl bis(4-methylbenzenesulfonate) (19 g, 45.6 mmol) potassium thioacetate (15.78 g, 3 eq) and DMF (70 mL). The mixture is allowed to stir at ambient temperature for 12 h. The red solution is diluted with ethyl acetate (200 mL) and the resulting solution is washed with a saturated aqueous $NaHCO_3$ solution and a saturated aqueous NaCl solution. The organic phase is dried over $MgSO_4$, filtered and concentrated on a rotary evaporator which resulted in the crude product as a red oil. It is purified by means of distillation. Yield: 8.1 g (80%)—yellow oil.

Second Step: Synthesis of S,S'-pentane-2,4-diyl bis(4-propylbenzothioate)

A 100 mL reaction vessel is charged with S,S'-pentane-2,4-diyl diethanethioate (5 g, 22.5 mmol) and methanol (50 mL). Sodium methoxide (2.57 g, 2.1 eq) is then slowly added at ambient temperature. The mixture is allowed to stir for 2 h. Methanol is removed by distillation and the resulting orange oil is diluted with pyridine (50 mL). It is cooled to 0° C. and 4-n-propyl-benzoyl chloride (11.08 g, 2.7 eq) is slowly added and stirred for 12 h. Pyridine is removed by distillation and the resulting oil is diluted with ethyl acetate (100 mL). The resulting solution is washed with a saturated aqueous NaHCO₃ solution and a saturated aqueous NaCl solution. The organic phase is dried over MgSO₄, filtered and concentrated on a rotary evaporator which resulted in the crude product as a yellow oil. It is purified by means of chromatography (SiO₂)-cyclohexane/ethyl acetate: 60/1. Yield: 4.4 g (45.6%).

Procedure for the Preparation of the Solid Catalyst Component Using Donors Ex 1-17.

Into a 500 mL round bottom flask, equipped with mechanical stirrer, cooler and thermometer 250 mL of TiCl₄ were introduced at room temperature under nitrogen atmosphere. After cooling to 0° C., while stirring, the internal donor and 10.0 g of the spherical adduct (prepared as described above) were sequentially added into the flask. The amount of charged internal donor was such to charge a Mg/donor molar ratio of 6. The temperature was raised to 100° C. and maintained for 2 hours. Thereafter, stirring was stopped, the solid product was allowed to settle and the supernatant liquid was siphoned off at 100° C. After the supernatant was removed, additional fresh TiCl₄ was added to reach the initial liquid volume again. The mixture was then heated at 120° C. and kept at this temperature for 1 hour. Stirring was stopped again, the solid was allowed to settle and the supernatant liquid was siphoned off.

The solid was washed with anhydrous hexane six times (6×100 mL) in temperature gradient down to 60° C. and one time (100 mL) at room temperature. The obtained solid was then dried under vacuum and analyzed.

Procedure for the Preparation of the Solid Catalyst Component Using Donor Ex 18.

Into a 500 mL round bottom flask, equipped with mechanical stirrer, cooler and thermometer 250 mL of TiCl₄ were introduced at room temperature under nitrogen atmosphere. After cooling to 0° C., while stirring, ethyl benzoate and 10.0 g of the spherical adduct (prepared as described above) were sequentially added into the flask. The amount of charged ethyl benzoate was such to charge a Mg/EB molar ratio of 4. The temperature was raised to 100° C. and maintained for 2 hours. Thereafter, stirring was stopped, the solid product was allowed to settle and the supernatant liquid was siphoned off at 100° C. After the supernatant was removed, additional fresh TiCl₄ was added to reach the initial liquid volume again followed by the addition of the internal donor with Mg/donor ratio of 6. The mixture was then heated at 120° C. and kept at this temperature for 1 hour. Stirring was stopped again, the solid was allowed to settle and the supernatant liquid was siphoned off. This last hot treatment at 120° C. for 1 hour is repeated an additional time. Stirring was stopped again, the solid was allowed to settle and the supernatant liquid was siphoned off.

The solid was washed with anhydrous hexane six times (6×100 mL) in temperature gradient down to 60° C. and one time (100 mL) at room temperature. The obtained solid was then dried under vacuum and analyzed.

General Procedure for the Polymerization of Propylene

A 4-liter steel autoclave equipped with a stirrer, pressure gauge, thermometer, catalyst feeding system, monomer feeding lines and thermostating jacket, was purged with nitrogen flow at 70° C. for one hour. Then, at 30° C. under propylene flow, were charged in sequence with 75 ml of anhydrous hexane, 0.76 g of AlEt₃, 0.076 g of dicyclopentyldimethoxysilane (D donor) and 0.006÷0.010 g of solid catalyst component. The autoclave was closed; subsequently 2.0 Nl of hydrogen were added. Then, under stirring, 1.2 kg of liquid propylene was fed. The temperature was raised to 70° C. in five minutes and the polymerization was carried out at this temperature for two hours. At the end of the polymerization, the non-reacted propylene was removed; the polymer was recovered and dried at 70° C. under vacuum for three hours. Then the polymer was weighed and fractionated with o-xylene to determine the amount of the xylene insoluble (X.I.) fraction.

TABLE 1

Composition and performance of exemplified catalysts

| Ex. | Internal Donor Structure/Name | Ti % wt | % wt | ED | Mileage kg/g | XI % wt | MIL g/10' |
|---|---|---|---|---|---|---|---|
| 1 | 2-(benzoylthio)-4-(tert-butyl)-3,6-dimethylphenyl benzoate | 11.6 | 4.3 | D | 62 | 98.6 | 1.8 |

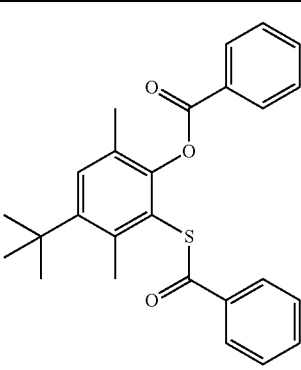

TABLE 1-continued

Composition and performance of exemplified catalysts

| Ex. | Internal Donor Structure/Name | Ti % wt | % wt | ED | Mileage kg/g | XI % wt | MIL g/10' |
|---|---|---|---|---|---|---|---|
| 2 | 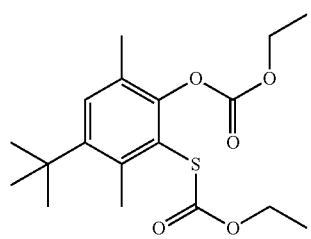 4-(tert-butyl)-2-((ethoxycarbonyl)thio)-6-methylphenyl ethyl carbonate | 18.3 | 3.4 | D | 37 | 97.5 | 2.9 |
| 3 | 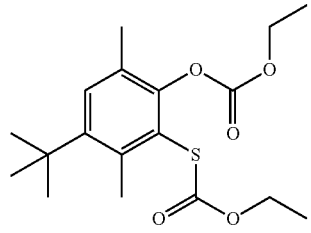 4-(tert-butyl)-2-((ethoxycarbonyl)thio)-3,6-dimethylphenyl ethyl carbonate | 18.1 | 3.5 | D<br>No ED | 41<br>80 | 98.2<br>94.3 | 3.6<br>4.7 |
| 4 | 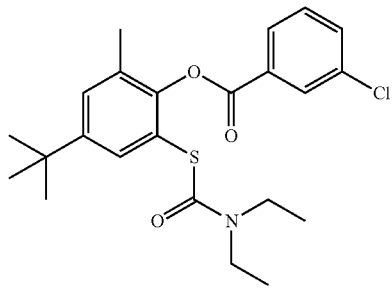 4-(tert-butyl)-2-((diethylcarbamoyl)thio)-6-methylphenyl 3-chlorobenzoate | n.d. | 4.5 | D | 80 | 97.3 | n.d. |
| 5 | 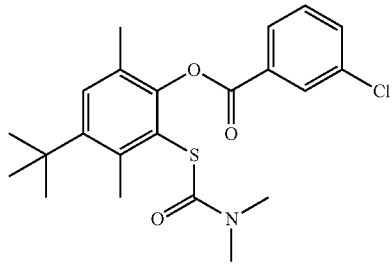 4-(tert-butyl)-2-((dimethylcarbamoyl)thio)-6-methylphenyl 3-chlorobenzoate | 15.0 | 4.0 | D | 81 | 96.4 | 2.1 |

TABLE 1-continued

Composition and performance of exemplified catalysts

| | Catalyst compostion | | | | Polymerization | | |
|---|---|---|---|---|---|---|---|
| | Internal Donor | | Ti | | Mileage | XI | MIL |
| Ex. | Structure/Name | % wt | % wt | ED | kg/g | % wt | g/10' |
| 6 | 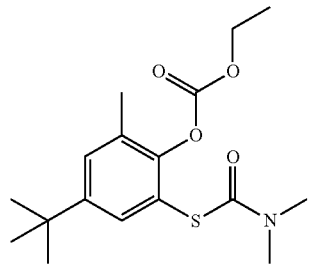<br>S-(5-(tert-butyl)-2-((ethoxycarbonyl)oxy)-3-methylphenyl) dimethylcarbamothioate | 15.9 | 4.2 | D | 71 | 97.8 | 2.3 |
| 7 | 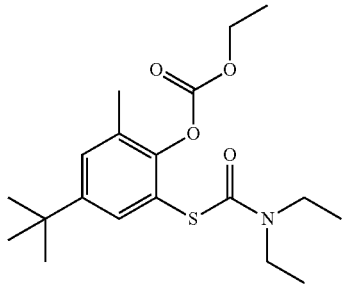<br>S-(5-(tert-butyl)-2-((ethoxycarbonyl)oxy)-3-methylphenyl) diethylcarbamothioate | 12 | 4.8 | D | 67 | 97.4 | n.d. |
| 8 | 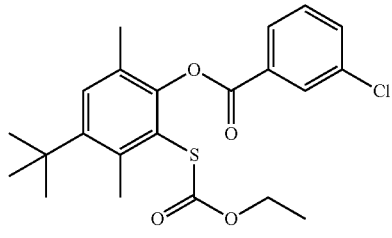<br>4-(tert-butyl)-2-((ethoxycarbonyl)thio)-3,6-dimethylphenyl 3-chlorobenzoate | n.d. | 3.6 | D | 42 | 98.6 | n.d. |
| 9 | 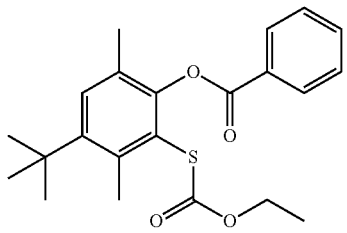<br>4-(tert-butyl)-2-((ethoxycarbonyl)thio)-3,6-dimethylphenyl benzoate | 14.7 | 4.0 | D | 70 | 98.9 | 2.2 |

TABLE 1-continued

Composition and performance of exemplified catalysts

| | Catalyst composition | | Ti | | Polymerization | | |
| --- | --- | --- | --- | --- | --- | --- | --- |
| | Internal Donor | | | | Mileage | XI | MIL |
| Ex. | Structure/Name | % wt | % wt | ED | kg/g | % wt | g/10' |
| 10 | 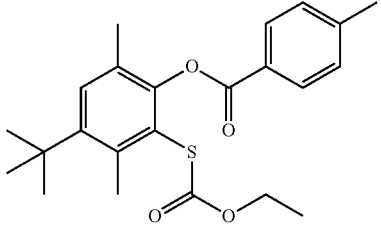 4-(tert-butyl)-2-((ethoxycarbonyl)thio)-3,6-dimethylphenyl 4-methylbenzoate | n.d. | 4.1 | D | 88 | 98.6 | 1.0 |
| 11 | 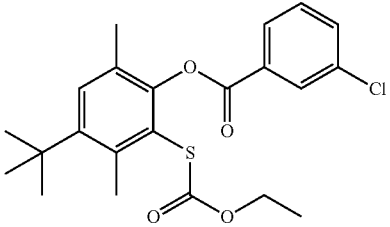 4-(tert-butyl)-2-((ethoxycarbonyl)thio)-6-methylphenyl 3-chlorobenzoate | 14.3 | 3.8 | D | 57 | 98.8 | 1.9 |
| 12 | 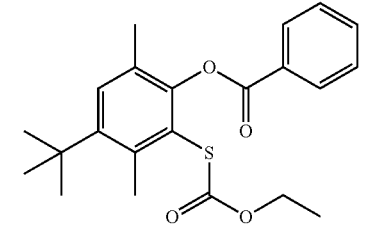 4-(tert-butyl)-2-((ethoxycarbonyl)thio)-6-methylphenyl benzoate | 16.4 | 4.4 | D | 66 | 98.1 | 2.6 |
| 13 | 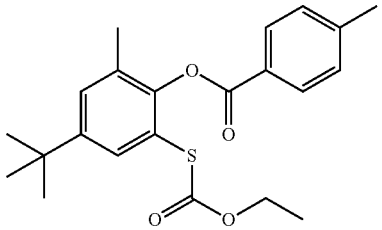 4-(tert-butyl)-2-((ethoxycarbonyl)thio)-6-methylphenyl 4-methylbenzoate | 10.6 | 3.5 | D | 76 | 98.3 | 1.5 |

TABLE 1-continued

Composition and performance of exemplified catalysts

| | Catalyst compostion | | Ti | | Polymerization | | |
| | Internal Donor | | | | Mileage | XI | MIL |
| Ex. | Structure/Name | % wt | % wt | ED | kg/g | % wt | g/10' |
|---|---|---|---|---|---|---|---|
| 14 | 4-(tert-butyl)-2-((ethoxycarbonyl)thio)-3,6-dimethylphenyl furan-2-carboxylate | n.d. | 3.7 | D | 55 | 97.8 | 3.0 |
| 15 | 4-(tert-butyl)-2-((ethoxycarbonyl)thio)-6-methylphenyl diethylcarbamate | n.d. | 5.0 | D | 71 | 97.2 | 5.7 |
| 16 | S-(5-cyclohexyl-2-((ethoxycarbonyl)oxy)-3-methylphenyl) dimethylcarbamothioate | 10.7 | 4.3 | D | 63 | 97.6 | 2.7 |
| 17 | syn S,S'-pentane-2,4-diyl dibenzothioate | n.d. | 3.7 | D | 28 | 97.4 | 2.1 |

TABLE 1-continued

Composition and performance of exemplified catalysts

| | Catalyst compostion | | | Polymerization | | |
|---|---|---|---|---|---|---|
| | Internal Donor | Ti | | Mileage | XI | MIL |
| Ex. | Structure/Name | % wt | % wt | ED | kg/g | % wt | g/10' |
| 18 | 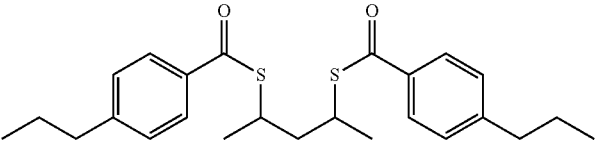<br>S,S'-pentane-2,4-diyl bis(4-propylbenzothioate) | n.d. | 4.0 | D | 73 | 97.1 | 1.7 |

ED: External Donor.
D: dicyclopentyldimethoxysilane

What is claimed is:

1. A solid catalyst component for the polymerization of olefins comprising Mg, Ti, Cl and at least an electron donor compound of formula (II)

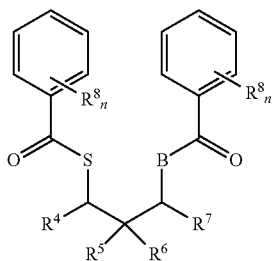

(II)

in which B is oxygen or sulphur S is sulfur, $R^4$-$R^7$ groups, equal to or different from each other, are hydrogen or $C_1$-$C_{15}$ hydrocarbon groups, optionally containing an heteroatom selected from halogen, P, S, N and Si, and $R^8$, equal to or different from each other, are selected from $C_1$-$C_{15}$ hydrocarbon groups which can be optionally linked to form a cycle and n is an integer from 0 to 5.

2. The solid catalyst component of claim 1 in which B is sulfur and $R^4$ and $R^7$ are selected from $C_1$-$C_{10}$ alkyl groups.

3. The solid catalyst component of claim 2 in which $R^4$ and $R^7$ are selected from from $C_1$-$C_5$ alkyl groups and $R^5$ and $R^6$ are selected from hydrogen or $C_1$-$C_{10}$ alkyl groups.

4. The solid catalyst component of claim 1 in which $R^8$ groups are independently selected from $C_1$-$C_{10}$ alkyl groups.

5. The solid catalyst component of claim 4 in which $R^8$ groups are independently selected from $C_1$-$C_5$ alkyl groups.

6. The solid catalyst component of claim 5 in which $R^8$ groups are independently selected from the group consisting of methyl, ethyl, n-propyl and n-butyl.

7. The solid catalyst component of claim 1 in which the index n ranges from 1 to 3.

8. The solid catalyst component of claim 7 in which the index n is 1.

9. The solid catalyst component of claim 1 in which the substituent $R^8$ is in position 4 of the benzoate ring.

10. A catalyst for the polymerization of olefins comprising the product of the reaction between:
    the solid catalyst component of claim 1,
    an alkylaluminum compound and optionally,
    an external electron donor compound.

11. A process for the (co)polymerization of olefins $CH_2$=CHR', in which R' is hydrogen or a hydrocarbyl radical with 1-12 carbon atoms, wherein the catalyst of claim 10 is contacted with the olefins in the gas phase in one or more fluidized or mechanically agitated bed reactors.

* * * * *